United States Patent [19]

Gravlee, Jr.

[11] 3,961,097

[45] June 1, 1976

[54] METHOD OF PREPARING TISSUE FOR MICROSCOPIC EXAMINATION

[76] Inventor: Joseph F. Gravlee, Jr., 2921 Balmoral Road, Birmingham, Ala. 25223

[22] Filed: Oct. 28, 1971

[21] Appl. No.: 193,563

[52] U.S. Cl.............................. 427/2; 424/3; 427/57
[51] Int. Cl.².................. A01N 1/00; B05D 3/12
[58] Field of Search.............. 117/3, DIG. 8, 113; 424/3; 427/2, 57

[56] References Cited

UNITED STATES PATENTS

| 3,098,370 | 7/1963 | Poole et al. | 117/DIG. 8 |
|---|---|---|---|
| 3,428,470 | 2/1969 | Welsh et al. | 117/3 |
| 3,553,311 | 1/1971 | Smith | 424/3 |
| 3,667,896 | 6/1972 | McCormick et al. | 117/3 |
| 3,679,450 | 7/1972 | Beightol | 117/3 |

OTHER PUBLICATIONS

*Revue Technique des Ind. du Cuir*, Mieczyslaw, vol. L, Dec. 1958, pp. 261–267.

Poston, *Am. Journ. of Med. Tech.*, vol. 31, July–Aug. 1965, pp. 279–284.

Poston, *Am. Journ. of Med. Tech.*, vol. 33, No. 4, July–Aug. 1967, pp. 263–268.

*Products Finishing*, "Ultrasonic Cleaning," Dec. 1968, pp. 58–70.

*Primary Examiner*—Harry J. Gwinnell
*Attorney, Agent, or Firm*—Stanley B. Kita

[57] ABSTRACT

In a process for preparing tissue for microscopic examination which process includes the steps of fixing a specimen of tissue, dehydrating the fixed specimen, clearing the dehydrated specimen, and impregnating the cleared specimen with paraffin, ultrasonic energy is applied to the specimen in each of the processing steps to reduce the total preparation time. Also, the time required to stain a specimen of tissue is reduced when ultrasonic energy is applied to the specimen while immersed in the stain.

6 Claims, No Drawings

METHOD OF PREPARING TISSUE FOR MICROSCOPIC EXAMINATION

The present invention relates to a method for processing a specimen of tissue for microscopic examination.

At present, two procedures are generally used in preparing specimens of tissue for microscopic examination. In one procedure a specimen is frozen, cut and mounted on a slide in an elapsed time of about 15 minutes. This so-called "frozen-section" procedure has the advantage of enabling a rapid histological diagnosis to be made from the specimen, and it is frequently employed in situations where a diagnosis is necessary while a patient is on an operating table. The procedure possesses certain disadvantages in that the prepared slide does not possess the uniformity of quality of slides prepared by other methods. Moreover, it is technically more difficult for serial sections of the same specimen to be examined by this procedure, and extreme caution must be exercised in cutting the specimen in order to ensure a sufficiently thin section and to avoid the possibility of damaging details of the specimen. The most serious objection of frozen section procedure is the necessity of preparing all the slides required for special stains and/or consultation and teaching purposes while the tissue is in the initial frozen state. If the tissue is thawed and refrozen for sectioning, it is severely damaged. Thus, when the frozen-section procedure is used in emergency situations, it is customary for another portion of the tissue specimen to be processed in the manner described hereinafter in order to have tissue available for additional sections if further examination becomes necessary.

In the other procedures, a slide of relatively high quality is produced when a section of the specimen is mounted in a block of paraffin; however, the time required to process a specimen of tissue for mounting in paraffin is on the order of several hours as compared with the minutes required to process a specimen by the frozen-section procedure. In the preparation of paraffin slides, a specimen of tissue is immersed initially in a fixing agent. The fixed specimen is then immersed in a dehydrating agent, and afterward the specimen is immersed in a clearing agent. Finally, the cleared specimen is immersed in a bath of paraffin which impregnates the specimen and permits it to be sliced into thin sections for subsequent mounting onto slides. Because of the length of time required to prepare specimens by this process, it is customary for hospital laboratories to begin processing the specimens late in the afternoon after surgeons have obtained specimens from their patients. The processing continues through the night, and slides of the specimens are available for microscopic examination the next morning. Although the slides produced according to this procedure are of higher quality than those produced by the frozen-section technique, the length of time required to process specimens is too great to enable this procedure to be used in situations where time is of the essence.

With the foregoing in mind, it is the primary object of the present invention to provide an improved method for preparing specimens of tissue for microscopic examination.

As a further object, the present invention provides a novel method by which tissue specimens of relatively high-quality can be processed for microscopic examination in a minimum amount of time.

More specifically, in the present invention, a slide of a specimen of tissue is prepared when a specimen is sequentially immersed in a fixing agent, a dehydrating agent, a clearing agent, and paraffin before being cut into thin sections and mounted onto slides. The time required to process the specimen is reduced when ultrasonic energy is applied to the specimen during each of the processing steps. Preferably, the specimen and processing agents are contained in a relatively small vessel which is immersed in a larger container containing a fluid, and the ultrasonic energy is applied to the fluid and hence to the agents and specimen. The intensity of application of the energy is controlled during the fixing step to ensure that cavitation does not occur within the bath. If desired, the intensity may be controlled by varying the quantity of fluid in the container.

These and other objects, features and advantages of the present invention should become apparent from the following description and examples.

In the conventional histopathology laboratory, specimens of tissue received from surgery or autopsy are trimmed and preserved in small containers of formaldehyde. The specimens are processed to remove water, and they are mounted in blocks of paraffin which are cut into thin sections. The thin sections are floated on water to enable them to be transferred to the slides, and the sections are securely mounted on the slides when they are heated. Thereafter, the paraffin around the mounted sections is removed, and the sections are stained to ready them for microscopic examination.

In the past, specimens of tissue were processed manually; however, because of the labor required to process the specimens, apparatus was developed to process the specimens automatically. A fine example of such apparatus is manufactured by the Technicon Instruments Corporation of Tarrytown, New York, and the apparatus is sold under the trade designation Ultra Autotechnicon. The apparatus comprises a housing in which is mounted a rotary conveyor carrying at peripherally-spaced locations a series of baskets for containing specimens of tissue during processing. Containers for various processing agents are mounted in the housing, and the containers are located below the path of movement of the baskets. There is provided means to raise and lower and to index the conveyor and baskets relative to the containers at various timed intervals which are programmed in a master control. In addition, means is provided to supply heat and vacuum in the housing, and means is provided to oscillate vertically the baskets in the containers to accelerate processing. After the specimens are loaded into the baskets and the master control set to the desired processing time, the apparatus is programmed to process automatically the tissue specimens.

The apparatus is capable of being programmed to process specimens for periods of time up to 16 hours. Various factors are considered in determining the length of time a specimen must be processed. A major factor is the thickness of the specimen; however, other factors such as the nature of tissue must be considered. When processing tissue in the aforementioned apparatus, the total recommended processing time corresponds substantially to the thickness of the specimen. Thus, for specimens 3, 4 or 5 millimeters thick, total processing times of 3, 4 or 5 hours, respectively, are required. However, dense tissue such as found in the muscle and connective tissue of the human uterus is particularly difficult to process and a longer processing time is recommended.

The apparatus is programmed to subdivide total processing time into increments so that each specimen spends a predetermined amount of time in each bath. In most instances, the specimen is sequentially immersed in a series of baths of the same agent in adjacent containers during a single step in the process. Thus, in processing a tissue specimen in the above apparatus, the specimen is loaded in one of the baskets, and the loaded basket is immersed sequentially in one or more baths of a fixing agent, a dehydrating agent, a clearing agent, and baths of liquified paraffin before being cut and stained and mounted onto a slide.

Although conventional agents may be used satisfactorily in the above process, slides of excellent quality are prepared when agents supplied by the manufacturer of the aforedescribed apparatus are used. In the fixing step, the preferred agent is a 10% solution of formalin in water; however, a 15% or 20% solution may be used satisfactorily. In the dehydrating and clearing steps, solutions designated as S-29 and UC-670, respectively, and supplied by Technicon, are preferred. If desired, an alcohol such as ethyl or isopropyl alcohol may be used satisfactorily as dehydrating agents. Also, xylene or cedar wood alcohol may be employed satisfactorily as clearing agents. In some laboratories dioxane or gasoline may be used as clearing agents; however, they are considered dangerous because of their toxic fumes and the danger of explosion. In the paraffin-impregnating step, paraffin of the usual laboratory grade is satisfactory.

In accordance with the present invention, it has been observed that the time required to process a specimen of tissue by the above process can be markedly reduced when ultrasonic energy is applied to the baths of agents containing the specimen in each step in the process. In applying the ultrasonic energy, the specimen of tissue is placed in a relatively small vessel containing a sufficient quantity of agent to cover the specimen, and the vessel is placed in a larger container having a quantity of fluid such as water. Ultrasonic energy is applied to the fluid in the larger container and is transferred through the fluid and the wall of the vessel into the agent surrounding the specimen. As a result, the agent in the vessel is agitated, and the time required for the agent to penetrate the specimen is reduced.

Although the intensity of application of ultrasonic energy to the specimen is not critical, it has been discovered that in the fixing step, the intensity must be maintained at a level below the level at which damage to cells in the tissue occurs. In ultrasonic generating apparatus of the type having a variable output, the intensity can be readily adjusted to the desired level. However, in apparatus having a fixed output intensity, it is desirable to control the intensity of application of ultrasonic energy by varying the level of the fluid in the larger container. Since the intensity is related inversely to the quantity of fluid in the container, the intensity is increased when the fluid level is reduced, and the intensity is decreased when the fluid level is increased. By thus controlling the intensity, potential damage to cells in the tissue specimen may be avoided.

Actual tests have established that tissue specimens prepared by the process of the present invention are at least equal in quality to tissue specimens prepared in the aforedescribed automatic apparatus. Moreover, the specimens are prepared in a fraction of the time. The following examples set forth the relative advantages of the present invention.

EXAMPLE I

A specimen 4 mm. thick of tissue from a rat which was fed a sugar-supplemented milk diet for 12 days was immersed in a solution of the fixing agent such as Bouin's solution, which contains picric acid. The fixed tissue was processed in the Ultra Autotechnicon using S-29 as the dehydrating agent and UC-670 as the clearing agent. The usual laboratory paraffin was used in the paraffin-impregnating bath. In the dehydrating step, the specimen was immersed sequentially in six baths of S-29, the duration of immersion for the first three baths being 10 minutes each and the duration of immersion for the last three baths being 20 minutes each. In the clearing step, three baths were used, the immersion time for the first two being 15 minutes each and the last being 20 minutes. In the paraffin-impregnating step, two baths were used, the immersion times being 20 and 40 minutes for the first and second baths, respectively. In the dehydrating and clearing steps, the temperatures of the baths were maintained between about 42° and 45° C. In the paraffin-impregnating step, the bath of paraffin was maintained at a temperature of about 68° C. The total processing time for the specimen, excluding the time in the fixing solution, was 3 hours and 20 minutes. When the resulting specimen was mounted on a slide and examined under a microscope, the specimen exhibited the customary quality.

Another specimen of tissue from the same rat was processed according to the method of the present invention. The specimen was fixed as described above, and the fixed specimen was immersed 3 times in a beaker of S-29 dehydrating agent for a period of 10 minutes each time. The dehydrating agent in the beaker was changed after each immersion. The dehydrated specimen was thereafter immersed twice in a beaker containing UC-670 clearing agent for periods of 5 and 10 minutes with the clearing agent being changed after each immersion. The cleared specimen was twice immersed in liquified paraffin for 5 and 10 minute periods with the paraffin being changed after each immersion. The beaker was immersed in a larger container of water after each change of agent, and ultrasonic energy was applied to the water in the container during the dehydrating, clearing and paraffin-impregnating steps. The energy was supplied by a 117 VAC, 60 cycle, 125 W. Bransonic$^R$ 220 generator. The total processing time, excluding fixing time, was 1 hour, and when the specimen was mounted on a slide and examined under a microscope, the specimen was of a quality at least as good as the specimen prepared by the automated apparatus.

EXAMPLE II

Specimens of tissue 4–5 mm thick from a human uterus and large intestine were processed using the same equipment as in Example I. The number of baths and the immersion times were varied. For instance, the specimens were immersed sequentially in 6 baths of dehydrating agent for a period of 1 hour each bath. The specimens were next immersed in two baths of clearing agent for 1 hour each bath. Thereafter, the specimens were immersed in two paraffin baths, 1 hour in the first bath and 3 hours in the second bath. The total processing time, excluding immersion in the fixing bath, was 12 hours. When the specimens were mounted in slides and examined, they exhibited the usual quality.

Like specimens of tissue were processed according to the method of the present invention. The specimens were immersed in five baths of the dehydrating agent, 10 minutes in the first bath and 5 minutes in each succeeding bath. The specimens were then immersed in two clearing and two paraffin baths for time periods of 7½ minutes each. Ultrasonic energy was applied as in Example I. The total processing time, excluding the fixing step, was 1 hour. When the specimens were mounted in slides and examined under a microscope, they exhibited a quality at least as good as the quality of the slides prepared according to the automated process.

EXAMPLE III

A specimen of tissue 1 millimeter thick from the liver of a rat was processed by each of the methods described in the foregoing examples using fresh tissue. In the Ultra Autotechnicon, the specimen was immersed for 10 minutes in the fixing agent and for six periods of 5 minutes each in the dehydrating agent. Thereafter, the specimen was immersed for three periods of 5 minutes each in the clearing agent. The specimen was finally immersed in the paraffin bath for periods of 5 and 10 minutes. The time required to process the tissue totaled 70 minutes. When the tissue specimen was mounted on a slide and examined under a microscope, it exhibited the customary quality.

A like specimen of the same tissue was processed according to the method of the present invention and with the fresh quantities of the processing agents as used above. The specimen was immersed in the fixing agent for 1 minute and then immersed in the dehydrating agent for 3 minutes. Thereafter, the specimen was immersed in the clearing agent for 1½ minutes, and the specimen was immersed for 1½ minutes in the paraffin bath. The total processing time was 7 minutes. When the specimen was mounted on a slide and viewed under a microscope, it exhibited at least the same quality as the specimen prepared by the conventional process.

Each of the specimens in the foregoing Examples I and II was immersed in a fixing agent prior to processing. In Example III, ultrasonic energy was also applied during the fixing step; however, it was observed that the intensity of the application of energy had to be controlled in order to avoid cavitation of the cells in the specimens. With the constant intensity apparatus used, the intensity of application of energy was controlled by varying the amount of water surrounding the beaker in the container. The intensity was reduced when the amount of water was increased, and the intensity was increased when the amount of water was reduced.

In order to avoid excessive cavitation of the solutions employed in the dehydrating and clearing steps, as well as the fixing step, the temperature was maintained below the 42°–45° C. range noted in Example I. The relatively low boiling points of the isopropyl alcohol and zylol constituents of these solutions necessitated accurate temperature control. The temperature of the paraffin bath was controlled at approximately 68° C. in order to maintain the paraffin in a liquid state.

Excessive cavitation can be determined by observing the formation of bubbles in the solutions. Once the tissue specimen is fixed, a small amount of bubbling of the solutions is permissible. However, during the fixing step, even less bubbling is permissible in the fixing solution if damage to the cells is to be avoided.

After the paraffin-impregnated specimens are mounted on slides, they are stained. One type of stain which is presently used is giemsa. It has been observed that staining time may be reduced by more than 50% when ultrasonic energy is applied to tissue specimens during immersion in the stain.

In addition to the foregoing uses of ultrasonic energy in the tissue-preparation process, it has been observed that the application of ultrasonic energy to fixing and developing solutions in the photographic development process produces significant improvements. For instance, it has been observed that the developing time is markedly reduced when ultrasonic energy is applied. Moreover, negatives from film which is developed in an ultrasonic process has a finer grain size than negatives from film developed otherwise. Hence, photographs printed from such negatives have a greater resolution than photographs produced by the conventional process.

In view of the foregoing, it should be apparent that the present invention provides a novel method for preparing specimens of tissue for microscopic examination in a minimum of time. Moreover, specimens of good quality can be produced in a relatively short time without the necessity of being processed in a vacuum.

While a preferred process has been described, various modifications, alterations and changes may be made without departing from the spirit and scope of the present invention as described in the appended claims.

I claim:

1. In a method of preparing a specimen of tissue for microscopic examination including the steps of: immersing a specimen in a bath of dehydrating agent; immersing the dehydrated specimen in a bath of clearing agent; and immersing the cleared specimen in a bath of paraffin, the improvement comprising: the step of applying ultrasonic energy to said specimen during each of said steps, whereby the time required to prepare said specimen is reduced.

2. A method according to claim 1 including the steps of immersing said specimen in a bath of fixing agent prior to said dehydrating step and applying ultrasonic energy to said specimen during immersion in said fixing bath.

3. A method according to claim 2 wherein each of said baths is disposed in a vessel and including the steps of immersing said vessel in a fluid contained in a container and applying said ultrasonic energy to said fluid, whereby the energy is transferred through the fluid and into the specimen in the vessel.

4. A method according to claim 3 including the step of controlling the intensity of the ultrasonic energy applied in said fixing step by adjusting the level of fluid in said container to maintain said intensity at a level below the level at which excessive cavitation occurs in said bath.

5. A method according to claim 4 including the step of controlling the temperature of said fluid in said dehydrating and clearing steps in correlation with the intensity of application of said ultrasonic energy to ensure the absence of excessive cavitation in said dehydrating and clearing baths.

6. A method according to claim 5 wherein the step of controlling the temperature of the fluid in correlation with the intensity of application of said ultrasonic energy includes the observation of the appearance of bubbles in said baths and controlling the level of fluid in the container in response to said observation.

* * * * *